United States Patent [19]
Fridge

[11] Patent Number: 5,638,461
[45] Date of Patent: Jun. 10, 1997

[54] STEREOSCOPIC ELECTRO-OPTICAL SYSTEM FOR AUTOMATED INSPECTION AND/OR ALIGNMENT OF IMAGING DEVICES ON A PRODUCTION ASSEMBLY LINE

[75] Inventor: David A. Fridge, Pasadena, Calif.

[73] Assignee: Kollmorgen Instrument Corporation, Chatsworth, Calif.

[21] Appl. No.: 631,042

[22] Filed: Apr. 12, 1996

Related U.S. Application Data

[63] Continuation of Ser. No. 255,673, Jun. 9, 1994, abandoned.

[51] Int. Cl.$^6$ .................................................. G06K 9/00
[52] U.S. Cl. ...................... 382/141; 382/154; 382/293; 348/190
[58] Field of Search .................................. 382/141, 148, 382/151, 154, 201, 276, 285, 287, 291, 293, 294, 295, 302; 348/47, 48, 92, 93, 180, 189, 190, 191

[56] References Cited

U.S. PATENT DOCUMENTS

| | | | |
|---|---|---|---|
| 4,654,872 | 3/1987 | Hisano et al. | 382/1 |
| 4,797,942 | 1/1989 | Burt | 382/1 |
| 4,969,106 | 11/1990 | Vogel et al. | 382/8 |
| 5,442,391 | 8/1995 | Hung et al. | 348/190 |

OTHER PUBLICATIONS

Advertisement of EeRise Corporation for ER9300 Monitor Auto Alignment System, Taipei Hsien, Taiwan, 6 pages, undated but reference made to late 1994 on p. 2, line 16.

*Primary Examiner*—Leo Boudreau
*Assistant Examiner*—Phuoc Tran
*Attorney, Agent, or Firm*—Townsend and Townsend and Crew LLP; Henry K. Woodward

[57] ABSTRACT

Disclosed is a stereoscopic optical inspection system. A computer uses the stereoscopic information to compute and correct for angular and distance misalignments between the unit-under-test and the inspection system. A feature of the optical system is the use of multiple high-resolution inspection cameras, in conjunction with a single stereoscopic reference camera. One example of a preferred embodiment is presented as an electro-optical inspection system for inspection and/or alignment of cathode-ray-tube displays and other video displays on a production assembly line.

7 Claims, 4 Drawing Sheets

STEREOSCOPIC ELECTRO-OPTICAL SYSTEM FOR AUTOMATED INSPECTION AND/OR ALIGNMENT OF IMAGING DEVICES ON A PRODUCTION ASSEMBLY LINE

This is a Continuation of application Ser. No. 08/255,673, filed Jun. 9, 1994, now abandoned.

BACKGROUND OF THE INVENTION

This invention relates generally to optical inspection systems, and more particularly the invention relates to a stereoscopic electro-optical system for automated inspection of visual displays.

Historically, inspection and alignment of high-precision image-producing displays, such a cathode-ray-tube (CRT), electroluminescent and liquid-crystal flat panel displays, were done by a skilled human operator with the assistance of various optical devices such as microscopes, photometers, overlay grids, and the like. This manual technique is inherently time-consuming and expensive if high quality results are required.

More recently, automated electro-optical systems have been developed to inspect and/or align image-producing displays. While much faster than manual methods, existing inspection systems are not capable of accurately performing inspection of display units-under-test (UUT) as they are delivered to the inspection station by a low-precision assembly line conveyor system, wherein the UUT may be misoriented relative to the inspection system in both angle and distance.

There are several known automated approaches that have been used in the past to make the required inspection and/or alignment. In "fixtured" electro-optical inspection systems, a mechanical fixturing system is used to precisely fix the inspection system relative to the display unit-under-test (UUT) while making the inspection. This method does not have the capability of making rapid inspection and/or alignment of the display UUT on a low-precision assembly line conveyor best, wherein the UUT may be misoriented relative to the inspection system in both angle and distance. In "feature-reference" electro-optical inspection systems, a specific feature which is always found on the UUT is used to compute a correction function which compensates for misalignment in angle and/or distance between the inspection system and the UUT. For example, one commercially available system looks for the bezel (frame) around the cathode-ray-tube display UUT while inspecting these UUTs on a conveyor belt. By assuming the bezel is of a known size and shape, this system deduces the distance and the orientation of the UUT and then generates a correction function for the inspection of the UUT. Unfortunately, this system is undesirably sensitive to minor differences in the size, shape, color, reflectivity and three-dimensional characteristics of the bezel. It is also not as accurate as is desirable for high-accuracy measurements of high-quality display UUTs.

Therefore, a primary purpose of this invention is to provide an electro-optical inspection and/or alignment system that is capable of making rapid measurements and/or electronic alignment of video display units as they are delivered to the inspection station without the necessity for human-handling, fixturing, or otherwise maintaining precise orientation of the display UUT while being relatively insensitive to variations in the angle and distance between the inspection system and the UUT.

SUMMARY OF THE INVENTION

The present invention is directed to a three-dimensional optical inspection system for adjustable visual displays and other objects. Briefly, a plurality of cameras are mounted in a spaced arrangement and oriented so that an object of interest is viewed by at least two cameras. Each camera is calibrated to define two-dimensional locations in the overlapping field of view. Computer means operates on the two-dimensional location in the overlapping field of view and determines three-dimensional locations of objects in the field of view.

Move particularly, in accordance with a preferred embodiment of the invention, each image frame of a camera has a plurality of pixels identified by row and column in the frame. Each pixel is associated with a line in space whereby a three-dimensional location of an object in the field of view is defined by the intersections of lines in space from the image frames of the plurality of cameras.

In accordance with features of the preferred embodiment, the calibration can be determined automatically, by viewing an object of known dimensions (i.e., an accurately known artwork image of cross-hatch lines), such that each pixel in the cameras field of view can be identified with a line in space.

In an embodiment for inspecting adjustable visual displays, the three dimensional coordinates of a location in the field of view are transformed to two-dimensional coordinates and the visual display is adjusted based on the transformed two-dimensional coordinates.

The invention and objects and features thereof will be more readily apparent from the following description and appended claims when taken with the drawing.

DETAILED DESCRIPTION OF THE ILLUSTRATIVE EMBODIMENTS

The invention is a unique stereoscopic optical inspection system, used in conjunction with a specially-programmed computer and/or system controller. The optical system can best be understood by referring to FIGS. 1 and 2.

Figure 1:
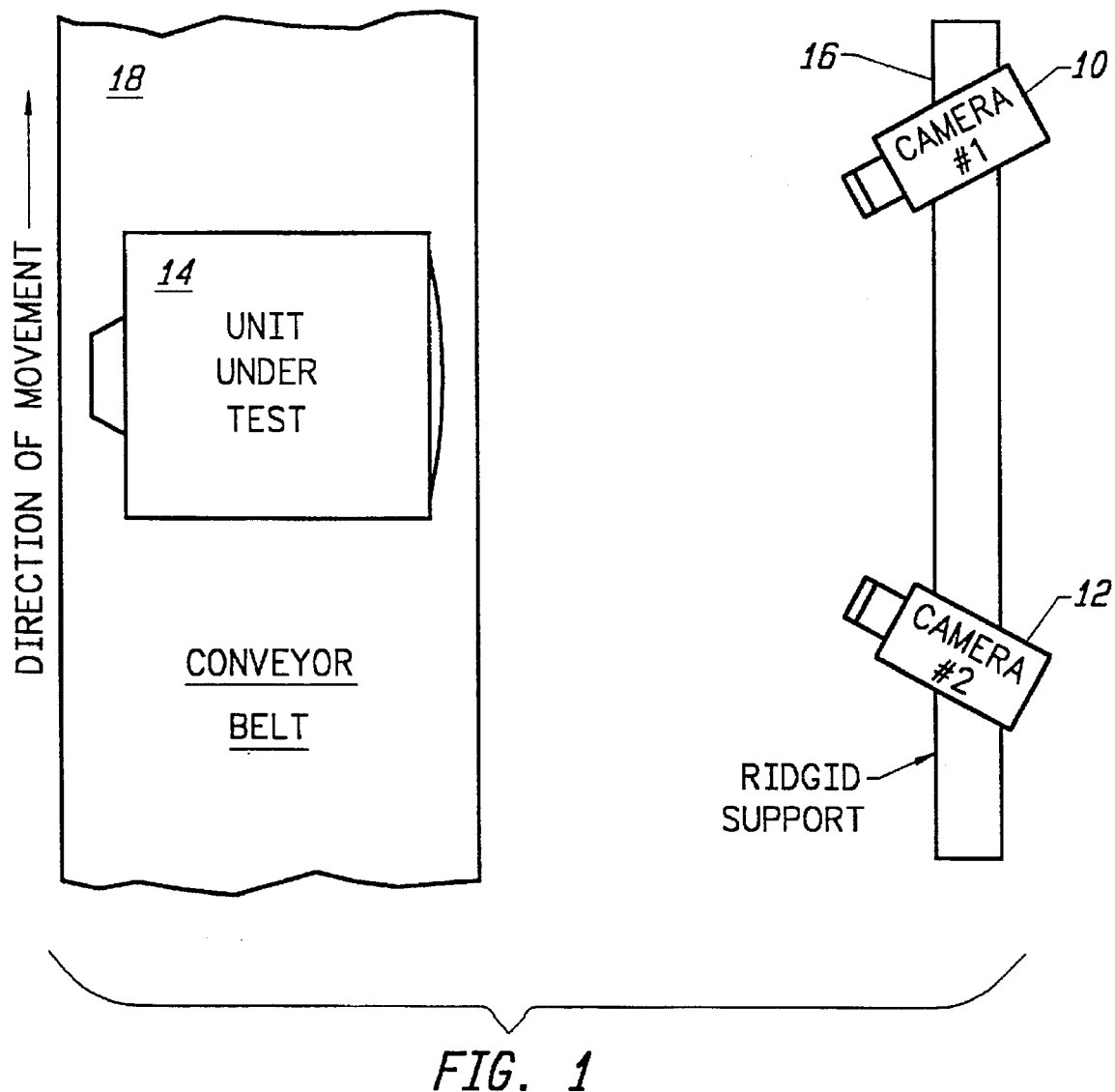
FIG. 1 is a schematic illustration of one embodiment of the invention.

FIG. 1 is a preferred embodiment consisting of two high-resolution inspection cameras 10, 12. The two cameras are aligned to provide complete overlap of the unit-under-test (UTT) 14. The two cameras are mounted on a rigid support 16, which maintains a known, fixed distance between the two cameras. Calibration software, using an accurately known artwork image, has established the position and perspective distortion associated with each camera. Consequently, when an actual display device 14 moving on belt 18 is presented to the system, each feature in the image displayed on the CRT can be viewed by both cameras, and a computer can calculate the three-dimensional coordinates of the feature. The complete three-dimensional map of the display surface is then rotated by the software to create an image of the UUT display image as it would appear to an "ideal observer" viewing the display from a perfectly centered location at a standard distance. Since the same viewing angle and distance are always mathematically reconstructed, regardless of the actual orientation of the UUT, all measurements made by the system are almost completely independent of the actual position and orientation of each display device as it is presented to the system.

Figure 2A:
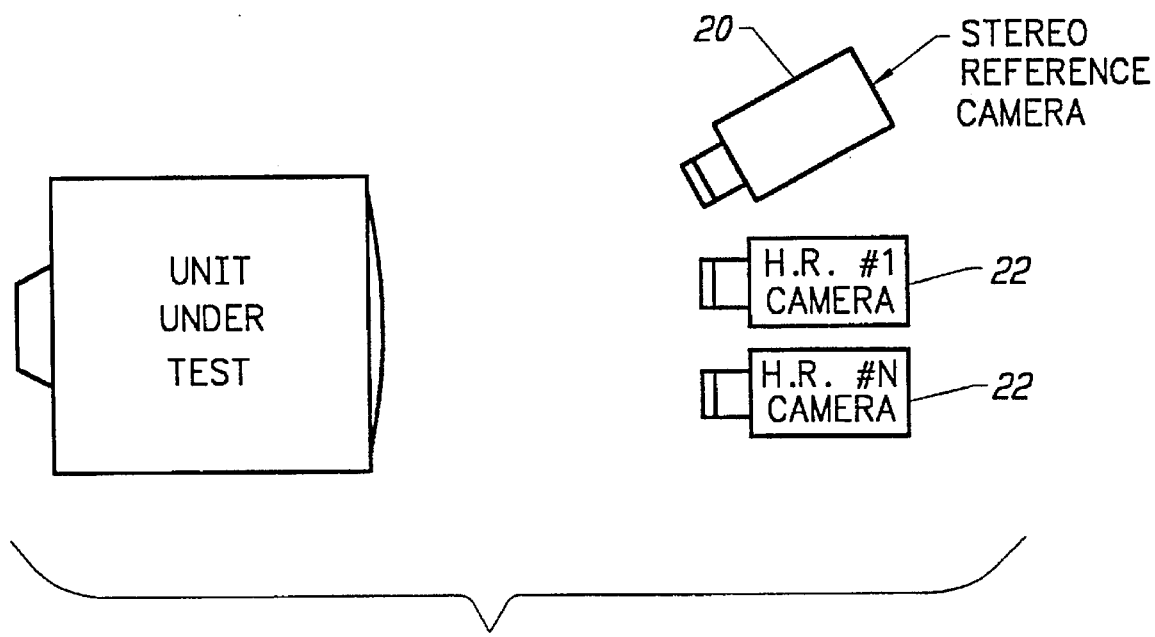
FIG. 2A is a schematic illustration of another embodiment of the invention.
Figure 2B:
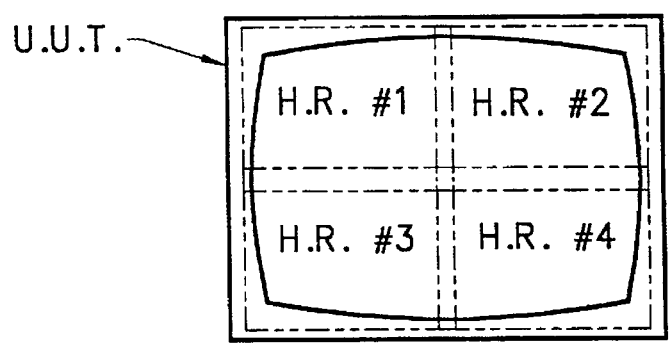
FIG. 2B illustrates field of view for cameras in FIG. 2A.

FIG. 2A is a simplified diagram of another embodiment of the invention. This consists of a single "stereoscopic reference camera" and an equal or larger number of high-resolution inspection cameras 22. The number, N, may be any number from one on up; four inspection cameras are shown in FIG. 2B. The number of high-resolution cameras are chosen to provide adequate spatial resolution for the type of UUT being inspected. In this embodiment, the output of the one stereoscopic reference cameras, which covers the entire field of view, is combined with the output of the "N" inspection cameras to provide the three-dimensional image data as described above. The single off-axis stereo reference camera provides enough depth information to accurately analyze the high resolution images provided by the "N" inspection cameras.

The output of the stereoscopic reference camera and the output of the one or more high-resolution inspection cameras are stored in one or more electronic memories or "frame grabbers" and then fed to a pre-programmed computer system. The images produced by the stereoscopic reference camera and the output of one or more of the other cameras must be combined to produce an accurate three-dimensional view of the pattern displayed by the UUT. In a preferred embodiment, this pattern is a crosshatch light or dark lines on a contrasting background. It is important for this calculation to have two different views of the same feature for analysis.

The first step in this analysis is to locate the same point of reference in both camera views. This location can be specified in terms of the pixel row and column in the frame at which it appears. Since a location identified by row and column is a two-dimensional measurement, the goal is to combine two two-dimensional measurements into one three-dimensional view. Important information is computed and saved during the calibration procedure which makes this procedure possible.

Essentially, the calibration data makes it possible to associate a particular line in space with each pixel in each camera's image space. This line is just the path of the ray of light which arrives at that pixel. Two camera views of the same object provide two intersecting lines, each passing through the object and the associated camera. The location in space where the lines intersect must be the three-dimensional coordinates of the object. In this way, the views of two or more cameras can be combined to give a three-dimensional representation of the UUT display.

After construction of a three-dimensional representation of the image displayed on the UUT, the system constructs a view of that image as seen from the ideal or standard viewpoint. Usually, this is a viewpoint centered directly over the central point of the UUT display area (i.e., looking "straight at" the display). The reconstruction of the view from this preferred viewpoint independent of the actual position and orientation of the UUT is the key to practical "fixtureless" inspection of the UUT display.

Figure 3:
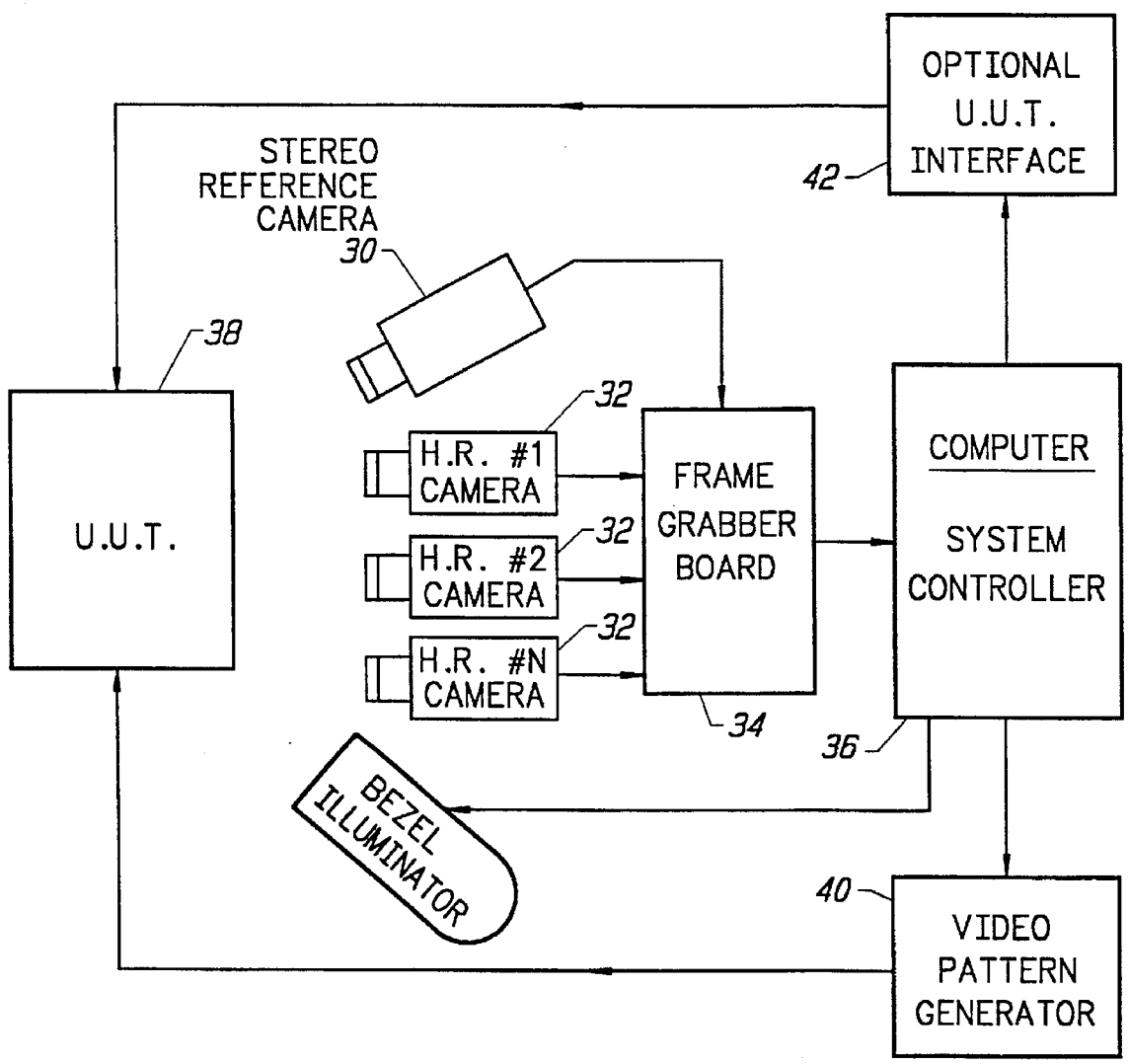
FIG. 3 is a functional block diagram of an optical inspection system in accordance with the invention.
Figure 4A:
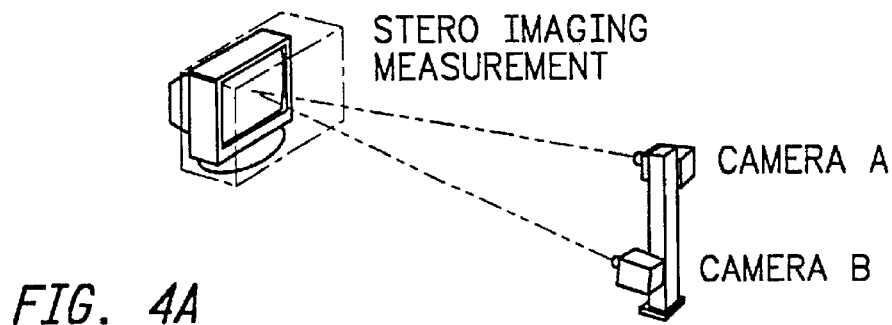
FIGS. 4A–4D illustrate operation of the embodiment of FIG. 1.
Figure 4B:
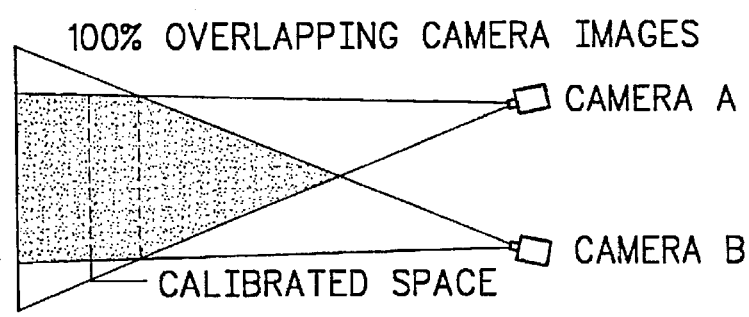
Figure 4C:
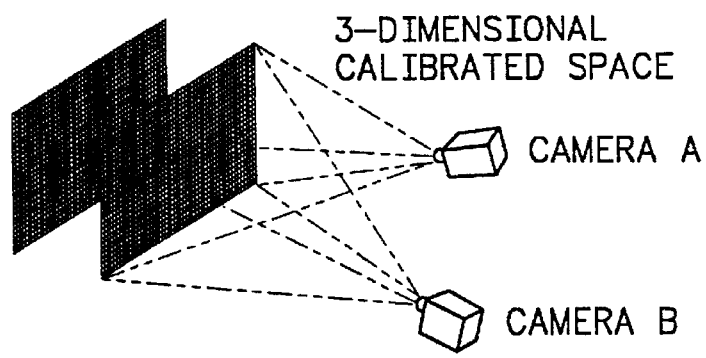
Figure 4D:
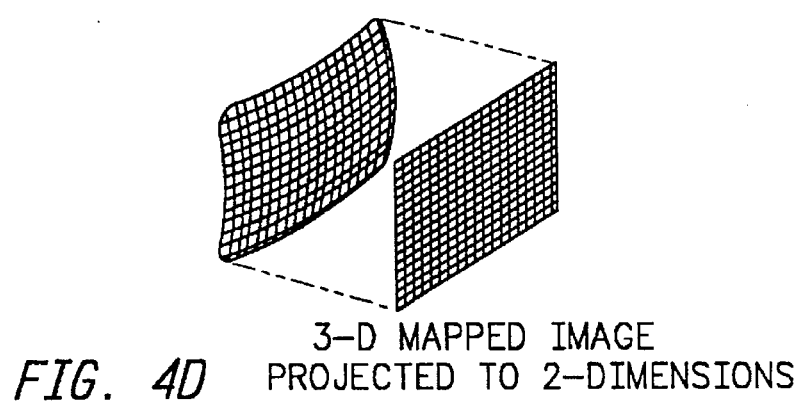

A preferred embodiment of the system is shown in FIG. 3. This figure is a schematic diagram of a system used to automatically inspect and/or align adjustable visual display in a production environment. The system consists of a stereoscopic reference camera 30 and "N" additional high-resolution inspection cameras 32, fed into a "frame grabber" 34 and a pre-programmed computer 36 as previously described. The computer also operates as a "system controller" to produce test patterns on the video monitor UUT 38, via a video pattern generator 40. Optionally, the system controller may also be used to align the UUT 38 via an electronic or electromechanical "UUT interface" 42. The controller may also be used to turn on or off a "bezel illuminator" light source, if necessary. The operator may interface with the computer system by any of a number of well-known means, such as a display CRT and a keyboard, mouse or touch-screen.

One preferred embodiment system is able to inspect visual displays in a production line in just 200 milliseconds (0.2 seconds). The optical system operates from a standoff distance of approximately one meter, and can compensate for misalignments as great as ±15° in tilt and ±125 mm in distance. The system typically produces accuracy better than 1° in tilt, and better than 1 mm in distance. Measurements of size and distortion on the UUT image are typically accurate to within a tenth of a millimeter.

FIGS. 4A–4D illustrate operation of the invention using the two camera embodiment of FIG. 1. As noted above, at the heart of the process of stereoscopic imaging is a procedure which translates the two views from separate cameras of the UUT into an accurate three-dimensional map of the UUT. Let us explain how this works by considering one single feature and show how the two views can be analyzed to give a three-dimensional location for this feature.

The first step in this analysis is to locate the same feature in both camera views. This location can be "specified in terms of the pixel row and column at which it appears. Since a location identified by row and column is a two-dimensional measurement, the goal is to combine two two-dimensional measurements into one three-dimensional view. Important information is computed and saved during the calibration procedure which makes this possible.

Since the camera's location in space is known (from calibration), and the direction of the ray of light from the camera to the actual feature we are measuring is known, we can specify mathematically the line which corresponds to that ray of light. What is unknown is where along that line the UUT is located. This can be computed because we have two different lines, one from each of our two cameras. The location where these two lines intersect is the correct location. That is our measurement of the X, Y, and Z coordinates of the feature we are trying to locate. A matter of practical interest is that generally, because of slight measurement errors, these lines do not actually intersect, but rather come very close to each other at one point. So to be precise, we choose as our best estimate of the true location the point of closest proximity of the rays from the two cameras. When this procedure is repeated for all the display points we wish to measure, we build up a three-dimensional map of the crosshatch image drawn inside the curved faceplate of the UUT.

The calibration process sets up a coordinate system with three perpendicular axes. Call them X, Y, and Z. By convention, X points to the left, Y is up, and Z points from the UUT generally toward the cameras. The X and Y directions are determined precisely by the lines on the calibration target, while Z is the direction perpendicular to a plane defined by X and Y. The calibration establishes the frame of reference in which the later measurements are made.

As a result of the calibration, the coordinates (in X, Y, and Z) of both cameras are known. Also computed is the absolute direction of the optical centerline of each camera.

In fact, each row and column location in each camera's image space can be associated with a line in space, or a ray of light, arriving at that camera from a particular direction. The important thing is that the calibration tells us the actual direction in space corresponding to each pixel in the camera's image.

One key element to system calibration is that cameras are arranged such that the images overlap 100% in the area where the UUT is to be measured. This allows the entire space in which the image is expected to appear to be mapped in three dimensions. The algorithm used to perform the three-dimensional measurements is made possible by a unique calibration technique, which is described briefly below.

Camera pixel size is mapped throughout the active field-of-view based on the known X, Y locations of the calibration target, such as a grid of intersecting lines, through a known distance, and re-measuring. Z-axis calibration is achieved in a second step by moving the calibration target through a known distance, and re-measuring. This allows the system to measure accurately anywhere within the three-dimensional volume of space defined by the camera overlap. The configuration used in FIGS. 4A–4D forms a 15"×20"×10" space, but can be easily varied by adjusting camera position and zoom to fit other UUT sizes.

Although the technique of measuring with three coordinate dimensions allows the characteristics of the UUT image to be analyzed independent of its orientation, a simple list of the raw coordinates in X, Y, and Z would not be very easily interpreted. Some means of simplifying the data, and relating them to an ideal display device is needed.

After the complexity of building up a complete three-dimensional representation of the displayed image, the next step is to reduce the data back into two dimensions. But this is really not wasted effort, because having the complete three-dimensional data allows us to translate into the very special two-dimensional representation we want. This is the two-dimensional space that would contain the display image if the UUT were ideally flat and truly square.

Imagine a plane which is parallel to the center of the UUT faceplate, whose horizontal axis is parallel to the top and bottom bezel, and whose vertical axis is at right angles to that. The origin of the coordinate system is in the exact center of the bezel opening. When the actual data from the faceplate image are mapped into that space, the image locations should be aligned to the coordinate axes, straight lines should be straight, and circles should be round. The two-dimensional space of the video image should map precisely into this special coordinate system, which makes the analysis of any distortion present in the display very simple.

Mathematically, what is being described is a coordinate transformation. The original measurements were made in an arbitrary coordinate system defined during calibration. We can bell this the system coordinates, and associate the coordinates with the letters X, Y, and Z. We wish to transform our data into a new coordinate system, with special relation to the actual position of the UUT. We call this the UUT coordinates, or (H, V, and Q). H is horizontal, relative to the bezel orientation, and V is vertical. Q is a measure of depth, but in the end the value for Q is just thrown away, because H and V tell us what we want to know about the display geometry.

The UUT coordinate system is convenient because it is easy to predict exactly where a particular pixel of the displayed image should appear. The location where the upper left corner of the display image should appear is always the same, and only one location is correct. In terms of (X, Y, and Z) this corner might appear almost anywhere, but in the special UUT coordinates, where is only one correct location for it, or any other pixel. This is why we transform our data into a special coordinate system that moves with the UUT bezel, and then project them into a flat, two-dimensional plane.

A typical installation provides a 20"×15"×10" calibrated volume of space, allowing accurate measurements to take place anywhere within that volume. For a typical 15" monitor, this results in freedom of positioning horizontally to +4.5", vertically to +3.5", and depth-wise (Z-axis) to +5". This would typically accommodate monitor sizes to 17" or 21", depending on the amount of freedom required for the production line. In addition, model changes in mixed-lines are accommodated in software, since the exact size of the UUT is measured.

There have been described several embodiments of the invention. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A three-dimensional optical inspection and alignment system for electronically adjustable visual displays on a production assembly line comprising a rigid support, two cameras mounted on said support, said cameras oriented to have an overlapping field of view with each camera being calibrated to define two-dimensional locations in said overlapping field of view, computer means for identifying calibrated two-dimensional locations of said visual displays in said overlapping field of view from said cameras, determining three-dimensional coordinates of said visual displays in said field of view, and transforming three-dimensional coordinates to two-dimensional coordinates in an ideal viewpoint, and means for electronically adjusting said visual displays based on said two dimensional coordinates.

2. The inspection system as defined by claim 1 and including a plurality of high resolution cameras and at least one stereo reference camera, said stereo reference camera viewing all of said field of view, and said plurality of high resolution cameras each covering a portion of said field of view and collectively covering all of said field of view.

3. The inspection system as defined by claim 1 and further including a frame grabber means for storing image frames from said plurality of cameras and providing said image frames to said computer means for identifying calibrated two-dimensional locations and determining three-dimensional locations of said objects.

4. The inspection system as defined by claim 3 wherein each image frame has a plurality of pixels each identified by row and column, each pixel being associated with a line in space, a three dimensional location of an object in said field of view being defined by the intersections of lines in space from said image frames.

5. A method of optically inspecting and aligning an electronically adjustable visual display on a production line comprising the steps of:

a) viewing said visual display with two rigidly mounted separated cameras having an overlapping field of view with each camera being calibrated to define two-dimensional locations in said overlapping field of view, b) determining three-dimensional locations of said visual display in said overlapping field of view from said two-dimensional locations, c) transforming said three-dimensional locations to a two-dimensional coordinate system, and d) electronically adjusting said display based on said two-dimensional coordinate system.

6. The method as defined by claim 5 wherein each frame of each camera has a plurality of pixels, each identified by row and column, each pixel being associated with a line in space, said step of determining three-dimensional locations including determining the intersections of lines in space from frames from said plurality of cameras.

7. A three-dimensional optical inspection and alignment system for electronically adjustable visual displays on a production assembly line comprising a rigid support, a plurality of cameras mounted on said support, said cameras oriented to have an overlapping field of view with each camera being calibrated to define two-dimensional locations in said overlapping field of view, said plurality of cameras including a plurality of high resolution cameras and at least one stereo reference camera, said stereo reference camera viewing all of said field of view, and said plurality of high resolution cameras each covering a portion of said field of view and collectively covering all of said field of view, computer means for identifying calibrated two-dimensional locations of said visual displays in said overlapping field of view from said cameras, determining three-dimensional coordinates of said visual displays in said field of view, and transforming three-dimensional coordinates to two-dimensional coordinates in an ideal viewpoint, a frame grabber means for storing image frames from said plurality of cameras and providing said image frames to said computer means for identifying calibrated two-dimensional locations and determining three-dimensional locations of said objects, and means for electronically adjusting said visual displays based on said two dimensional coordinates.

* * * * *